United States Patent
Higuchi (10) Patent No.: US 10,261,060 B2
(45) Date of Patent: Apr. 16, 2019

(54) SENSOR CONTROL APPARATUS AND GAS DETECTION SYSTEM

(71) Applicant: NGK SPARK PLUG CO., LTD., Nagoya-shi, Aichi (JP)

(72) Inventor: Yuzo Higuchi, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 216 days.

(21) Appl. No.: 15/168,927

(22) Filed: May 31, 2016

(65) Prior Publication Data
US 2016/0356753 A1    Dec. 8, 2016

(30) Foreign Application Priority Data

Jun. 8, 2015  (JP) ................................ 2015-115835

(51) Int. Cl.
*G01N 33/00*    (2006.01)
*G01N 27/406*   (2006.01)
*G01N 27/419*   (2006.01)

(52) U.S. Cl.
CPC ..... *G01N 33/0073* (2013.01); *G01N 27/4065* (2013.01); *G01N 27/419* (2013.01); *G01N 33/0036* (2013.01)

(58) Field of Classification Search
CPC .. G01N 27/409; G01N 27/4065; G01N 27/41; G01N 27/419; G01N 33/0073; G01N 33/0036

USPC ......................................... 701/109; 73/23.32
See application file for complete search history.

(56) References Cited

U.S. PATENT DOCUMENTS

| | | | |
|---|---|---|---|
| 8,679,312 B2 | 3/2014 | Inoue et al. | |
| 2002/0162743 A1* | 11/2002 | Inagaki | G01N 27/4065 204/425 |
| 2010/0122568 A1* | 5/2010 | Inoue | G01N 27/4065 73/31.05 |

FOREIGN PATENT DOCUMENTS

JP          4954185 B2      6/2012

* cited by examiner

*Primary Examiner* — Lisa M Caputo
*Assistant Examiner* — Irving A Campbell
(74) *Attorney, Agent, or Firm* — Sughrue Mion, PLLC (57) ABSTRACT

A sensor control apparatus controls a gas sensor including an electromotive force cell (a detection cell) and an oxygen pump cell. The sensor control apparatus includes an AD conversion section (31); a PID computation section (61); a first signal generation section (63) which generates a DAC control signal S1 (a pump current control signal) based on the results of PID performed by the PID computation section (61); a current DA conversion section (35); and a first signal generation section (63), a second signal generation section (65), and a signal output section (67) configured to selectively set a combination of the results of the computations performed by the PID computation section (61) and to generate a gas detection signal S2 based on the set combination of the computation results.

4 Claims, 3 Drawing Sheets

SENSOR CONTROL APPARATUS AND GAS DETECTION SYSTEM

BACKGROUND OF THE INVENTION

1. Field of the Invention

The present invention relates to a sensor control apparatus and to a gas detection system.

2. Description of the Related Art

A sensor control apparatus has been known for controlling a gas sensor having a detection cell and an oxygen pump cell, and a gas detection system which includes the gas sensor and the sensor control apparatus. The detection cell of the gas sensor produces an electromotive force corresponding to a particular component contained in an object gas that has been introduced into an interior chamber of the gas sensor, and the oxygen pump cell pumps oxygen into or out of the object gas in accordance with a pump current.

An example of such a gas sensor is an A/F sensor (oxygen sensor) which pumps oxygen into or out of an object gas that has been introduced into an interior chamber of the gas sensor through the use of an oxygen pump cell. The electromotive force produced by such a detection cell becomes equal to a target voltage set in advance, and which linearly detects the concentration of oxygen contained in the object gas based on the pump current flowing (supplied) to the oxygen pump cell at that time. Another example of such a gas sensor having an oxygen pump cell is an NOx sensor for detecting the concentration of NOx contained in an object gas.

Such a sensor control apparatus must have various computation functions for controlling the pump current. For example, Patent Document 1 discloses a sensor control apparatus which includes a PID computation section for performing PID computation processing (proportional computation processing, integral computation processing, and differential computation processing) on an electromotive force signal (detection voltage output from the detection cell) which changes with the electromotive force of the detection cell. This sensor control apparatus feedback-controls the detection cell by computing and controlling a control value for controlling the supply of pump current based on the PID computation result output from the PID computation section such that the detection voltage becomes equal to a predetermined target voltage.

[Patent Document 1] Japanese Patent No. 4954185

3. Problems to be Solved by the Invention

In the above-described sensor control apparatus, the control value for controlling the supply of pump current, which value is computed based on the PID computation results output from the PID computation section, is utilized as a sensor output signal (gas detection signal) as is, and the particular component contained in the object gas is detected based on the signal.

Depending on a user's need, application, etc., a noise-reduced gas detection signal is desirably used for detecting the particular component contained in the object gas (hereinafter also referred to as "gas detection"), or a highly responsive gas detection signal is desirably used for the gas detection. However, the above-described sensor control apparatus operates on the premise that the control signal based on the proportional computation result, the integral computation result, and the differential computation result output from the PID computation section is utilized as is for gas detection. Therefore, the above-described sensor control apparatus encounters difficulty in using a gas detection signal suitable for the user's need, application, etc., and has a low degree of versatility.

SUMMARY OF THE INVENTION

In view of the foregoing, an object of the present invention is to provide a sensor control apparatus which allows selective use of different types of gas detection signals for gas detection in accordance with a user's need, application, etc., and which has a high degree of versatility. Another object of the present invention is to provide a gas detection system which includes such a sensor control apparatus.

The above objects have been achieved by providing (1) a sensor control apparatus for controlling a gas sensor including a detection cell which produces an electromotive force corresponding to a particular component contained in an object gas and an oxygen pump cell which pumps oxygen into or out of the object gas that has been introduced into an interior chamber of the gas sensor in accordance with a pump current. The sensor control apparatus comprises an analog-to-digital conversion section which converts an analog electromotive force signal changing with the electromotive force of the detection cell to a digital electromotive force signal; a PID computation section which digitally performs proportional computation processing, integral computation processing, and differential computation processing on the digital electromotive force signal; a pump current control signal generation section which generates a digital pump current control signal for controlling the pump current such that the digital electromotive force signal assumes a predetermined target value, based on the results of the proportional computation, the integral computation, and the differential computation performed by the PID computation section; a digital-to-analog conversion section which converts the digital pump current control signal to an analog signal; and a gas detection signal generation section configured to selectively set one combination or a plurality of combinations of the results of the proportional computation, the integral computation, and the differential computation performed by the PID computation section, and to produce one or a plurality of gas detection signals for detection of the particular component contained in the object gas based on the set combination or plurality of set combinations of the computation results.

In the above-described sensor control apparatus, the gas detection signal generation section selectively sets one combination or a plurality of combinations of the three computation results (the proportional computation result, the integral computation result, the differential computation result) obtained as a result of the computation processing performed by the PID computation section. The gas detection signal generation section produces one or a plurality of gas detection signals for detection of the particular component contained in the object gas based on the set combination of the computation results.

Namely, the gas detection signal generation section can produce a plurality of types of gas detection signals based on the three computation results provided from the PID computation section and combinations of the computation results. Therefore, it becomes possible to freely select an optimum gas detection signal from the plurality of types of gas detection signals in accordance with a user's need, application, etc. As a result, the degree of versatility of the sensor control apparatus is increased.

For example, in the case where high responsiveness is required in the gas detection, it is advantageous to select and use a gas detection signal which is produced based on the three computation results (the proportional computation result, the integral computation result, and the differential computation result) as in the case of the pump current control signal used for control of the pump current. In the case where noise reduction is required, it is advantageous to select and use a gas detection signal which is produced based on the computation results, excluding the differential computation result (leaving the proportional computation result and the integral computation result). As described above, it becomes possible to select the gas detection signal to be used for gas detection in accordance with a user's need, application, etc. Therefore, the degree of versatility of the sensor control apparatus is increased.

Also, the pump current control signal generation section produces the pump current control signal used for control of the pump current supplied to the oxygen pump cell. The pump current control signal is a signal produced based on the three computation results (the proportional computation result, the integral computation result, and the differential computation result) obtained as a result of the computation processing of the PID computation section. Therefore, by supplying to the oxygen pump cell the pump current generated based on the pump current control signal, the pumping of oxygen into or out of the object gas that has been introduced into an interior chamber of the gas sensor can be performed properly in accordance with the state of change in the electromotive force of the detection cell.

As a result, in the sensor control apparatus, for the control of the pump current of the oxygen pump cell, so as to render the electromotive force coincident with a target voltage, the pump current control signal suitable for that control can be used. Also, for detection of the particular component contained in the exhaust gas (gas detection), an optimum gas detection signal can be freely selected and used from the plurality of types of gas detection signals in accordance with a user's need, application, etc.

Also, since the sensor control apparatus has a digital control section (digital circuit), a change of controller constants becomes easier as compared with the case where the sensor control apparatus has an analog circuit. Therefore, it becomes easier to control a greater number of types of gas sensors having various characteristics. In particular, it is possible to easily realize a configuration which allows selective use of different types of gas detection signals for gas detection in accordance with a user's need, application, etc.

In a preferred embodiment (2), the gas detection signal generation section produces the gas detection signal based on the combination including at least the result of the integral computation among the results of the proportional computation, the integral computation, and the differential computation performed by the PID computation section. In this case, since the gas detection signal is a signal produced based on the computation result containing the integral computation result, the particular component contained in the object gas can be detected accurately based on the state of change in the electromotive force of the detection cell over a long period of time.

In another aspect (3), the present invention provides a gas detection system which comprises a gas sensor including a detection cell which produces an electromotive force corresponding to a particular component contained in an object gas that has been introduced into an interior chamber of the gas sensor and an oxygen pump cell which pumps oxygen into or out of the object gas in accordance with a pump current; and the sensor control apparatus described in (1) or (2) above.

The gas detection system (3) includes the above-described sensor control apparatus (1) or (2). Therefore, like the above-described sensor control apparatus, the gas detection system allows selective use of different types of gas detection signals for gas detection in accordance with a user's need, application, etc. As a result, the degree of versatility of the gas detection system is increased.

As described above, the present invention can provide a sensor control apparatus which allows selective use of different types of gas detection signals for gas detection in accordance with a user's need, application, etc., and which has a high degree of versatility, and a gas detection system including the sensor control apparatus.

DESCRIPTION OF REFERENCE NUMERALS

Reference numerals used to identify various features in the drawings include the following.
1: gas detection system
2: sensor control apparatus
14: pump cell (oxygen pump cell)
24: electromotive force cell (detection cell)
31: AD conversion section (analog-to-digital conversion section)
35: current DA conversion section (digital-to-analog conversion section)
61: PID computation section
63: first signal generation section (pump current control signal generation section, gas detection signal generation section)
65: second signal generation section (gas detection signal generation section)
67: signal output section (gas detection signal generation section)
8: gas sensor
S1: DAC control signal (pump current control signal)
S2: gas detection signal
Vs: detection voltage (electromotive force signal)

DETAILED DESCRIPTION OF THE PREFERRED EMBODIMENTS

Embodiments to which the present invention is applied will be described in detail with reference to the drawings. However, the present invention should not be construed as being limited thereto.

That is, the present invention is not limited to the following embodiments, and various forms may be employed so long as they fall within the technical scope of the present invention.

First Embodiment

Figure 1:
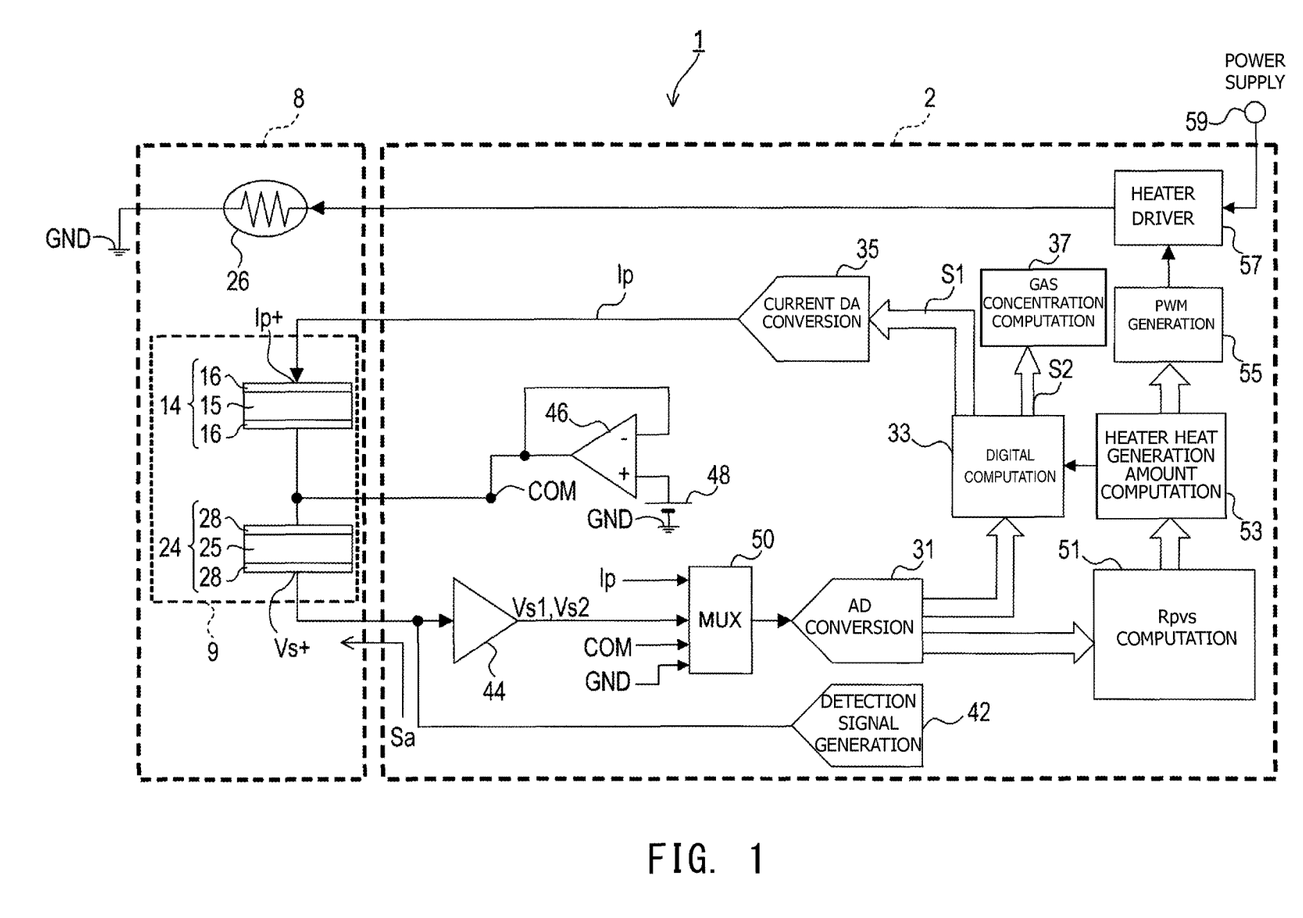
FIG. 1 is an overall diagram of a gas detection system.

<1-1. Overall Configuration>
FIG. 1 is an overall diagram of a gas detection system 1 which is an embodiment of the present invention.

The gas detection system 1 is used, for example, for the purpose of detecting a particular gas (oxygen in the present embodiment) contained in exhaust gas discharged from an internal combustion engine.

The gas detection system 1 includes a gas sensor 8 for detecting oxygen and a sensor control apparatus 2 for controlling the gas sensor 8. The gas detection system 1 reports the detected oxygen concentration to an engine control apparatus (not shown).

The engine control apparatus is a microcontroller which executes various types of control processing for controlling the internal combustion engine. As one of the various types of control processing, the engine control apparatus executes air-fuel ratio control for the internal combustion engine while using the oxygen concentration detected by the gas detection system 1.

The gas sensor 8 is provided on an exhaust pipe of the internal combustion engine (engine) and is used to detect the concentration of oxygen contained in exhaust gas over a wide oxygen concentration range. The gas sensor 8 is also called a linear lambda sensor. The gas sensor 8 is composed of a sensor element 9 and a heater 26.

The sensor element 9 is composed of a pump cell 14 and an electromotive force cell 24.

The pump cell 14 includes an oxygen-ion-conducting solid electrolyte body 15 formed of partially-stabilized zirconia ($ZrO_2$), and a pair of porous electrodes 16 mainly formed of platinum and provided on the front and back surfaces of the solid electrolyte body 15. The electromotive force cell 24 includes an oxygen-ion-conducting solid electrolyte body 25 formed of partially-stabilized zirconia ($ZrO_2$), and a pair of porous electrodes 28 mainly formed of platinum and provided on the front and back surfaces of the solid electrolyte body 25.

The heater 26 is composed of a heating resistor which produces heat when externally energized. The heater 26 heats the pump cell 14 and the electromotive force cell 24, thereby bringing them into an activated state.

Notably, the gas sensor 8 includes a measurement chamber (not shown) between the pump cell 14 and the electromotive force cell 24, and which is located inside the gas sensor 8. An object gas (exhaust gas in the present embodiment) is introduced into the measurement chamber through a porous diffusion layer (not shown).

Using the electromotive force cell 24, the gas sensor 8 generates an electromotive force (detection voltage Vs) corresponding to the oxygen concentration in the measurement chamber (in other words, the oxygen concentration of the object gas introduced into the measurement chamber through the porous diffusion layer). Specifically, the electromotive force cell 24 generates a detection voltage Vs corresponding to the difference in oxygen concentration between the front and back porous electrodes 28 of the electromotive force cell 24. Namely, the detection voltage Vs output from the electromotive force cell 24 changes with the oxygen concentration in the measurement chamber.

Using the pump cell 14, the gas sensor 8 pumps oxygen out of the object gas contained within the measurement chamber and pumps oxygen into the measurement chamber such that the detection voltage Vs from the electromotive force cell 24 becomes equal to a predetermined reference value (e.g., 450 mV). Specifically, a pump current Ip is caused to flow between the front and back porous electrodes 16 of the pump cell 14 so as to pump oxygen into and out of the measurement chamber, thereby adjusting the oxygen concentration in the measurement chamber.

Namely, the gas sensor 8 is used for an application in which the concentration of oxygen contained in the object gas is detected based on the pump current Ip applied to the pump cell 14 such that the oxygen concentration in the measurement chamber becomes equal to a predetermined target concentration (e.g., an oxygen concentration corresponding to the stoichiometric air-fuel ratio).

The sensor control apparatus 2 determines the oxygen concentration of the exhaust gas by driving and controlling the gas sensor 8, and notifies the engine control apparatus (not shown) of the determined oxygen concentration.

The sensor control apparatus 2 includes an AD conversion section 31 (analog-to-digital conversion section 31), a digital computation section 33, a current DA conversion section 35 (current digital-to-analog conversion section 35), a gas concentration computation section 37, a detection signal generation section 42, a buffer 44, an operational amplifier 46, a reference voltage generation section 48, a multiplexer 50, an Rpvs computation section 51, a heater heat generation amount computation section 53, a PWM generation section 55, and a heater driver 57.

The detection signal generation section 42 inputs to the electromotive force cell 24 of the gas sensor 8 an impedance detection signal Sa for detecting the internal resistance of the electromotive force cell 24 of the gas sensor 8. Specifically, the detection signal generation section 42 supplies a constant current to the electromotive force cell 24 as the impedance detection signal Sa in response to an instruction from the digital computation section 33.

The buffer 44 detects the voltage between opposite ends of the electromotive force cell 24 at high impedance, and outputs the voltage to the multiplexer 50 at low impedance. Notably, when the impedance detection signal Sa is not input, the voltage between opposite ends of the electromotive force cell 24 becomes an output signal Vs1 (detection voltage Vs) which changes with the oxygen concentration in the measurement chamber. In contrast, when the impedance detection signal Sa is input, the voltage between the opposite ends of the electromotive force cell 24 becomes a response signal Vs2 which changes with the internal resistance of the electromotive force cell 24.

The operational amplifier 46 sets the potential of a common terminal COM, to which the pump cell 14 and the electromotive force cell 24 are connected, to a predetermined potential. Specifically, the operational amplifier 46 sets the potential of the common terminal COM to a potential which is determined based on the output voltage (2.5 V in the present embodiment) of the reference voltage generation section 48 with the ground potential GND used as a reference. Notably, in the present embodiment, the ground potential GND corresponds to the reference potential of the sensor control apparatus 2.

The multiplexer 50 (hereinafter also referred to as the MUX 50) outputs one of the plurality of received analog signals to the AD conversion section 31. The multiplexer 50 determines which one of the analog signals is to be output based on an instruction from the digital computation section 33.

The plurality of analog signals input to the multiplexer 50 includes "voltage between the Vs+ terminal of the electromotive force cell 24 and the common terminal COM" (Vs+-COM voltage), "voltage between the Ip+ terminal of the pump cell 14 and the ground potential GND" (Ip+-GND voltage), "voltage between the common terminal COM and the ground potential GND" (COM-GND voltage), and "voltage between the Vs+ terminal of the electromotive force cell 24 and the ground potential GND (Vs+-GND voltage). Notably, the Vs+ terminal and the common terminal COM correspond to the two electrode terminals of the electromotive force cell 24, and the Ip+ terminal and the common terminal COM correspond to the two electrode terminals of the pump cell 14.

The multiplexer 50 includes a plurality of changeover switch sections (not shown) disposed on connection paths between a plurality of input terminals and a single output terminal. The states (ON/OFF states) of the plurality of changeover switch sections are set based on the instruction from the digital computation section 33, whereby the multiplexer 50 can output one of the plurality of received analog signals. In the present embodiment, the multiplexer 50 receives a plurality of analog signals and outputs the plurality of analog signals one by one in a predetermined order.

The AD conversion section 31 converts the analog signal output from the multiplexer 50 to a digital signal, and sends the digital signal to the digital computation section 33 and the Rpvs computation section 51.

The digital computation section 33 performs computation control processing, such as sensor control processing and pump current control processing. The pump current control processing will be described below.

The sensor control apparatus 2 includes an unillustrated EEPROM and an unillustrated RAM.

The EEPROM is a storage section which stores the contents of the computation control processing, various parameters used for the computation control processing, and others. In addition, the EEPROM stores various information (e.g., the maximum permissible current of the pump cell 14, etc.) determined in accordance with the type and characteristics of the gas sensor 8, which is a controlled object. This information is stored in the EEPROM during the fabrication of the sensor control apparatus 2.

The RAM is a storage section which temporarily stores control data, etc., and is used for various kinds of computation control processing.

The current DA conversion section 35 receives the DAC control signal S1 which contains information (e.g., supply direction and current value) of a control value for controlling the supply of the pump current Ip (hereinafter referred to as the "the supply control value for the pump current Ip") which is computed by the digital computation section 33, converts the received digital signal to an analog signal, and supplies to the pump cell 14 a pump current Ip determined based on the DAC control signal S1.

The gas concentration computation section 37 computes the concentration of a particular gas (oxygen) contained in exhaust gas based on the gas detection signal S2 which contains information regarding the supply control value for the pump current Ip computed by the digital computation section 33.

Namely, the gas concentration computation section 37 computes the concentration of oxygen contained in the object gas based on the pump current Ip supplied to the pump cell 14 such that the oxygen concentration in the measurement chamber becomes equal to the predetermined target concentration (e.g., an oxygen concentration corresponding to the stoichiometric air-fuel ratio).

The Rpvs computation section 51 computes the internal resistance Rpvs of the electromotive force cell 24 based on the response signal Vs2 and the output signal Vs1 received from the AD conversion section 31.

The heater heat generation amount computation section 53 digitally computes the temperature of the gas sensor 8 based on the internal resistance Rpvs computed by the Rpvs computation section 51, and computes a heater heat generation amount which is necessary to make the computed temperature approach the sensor target temperature or maintain the computed temperature at the sensor target temperature.

The PWM signal generation section 55 computes the duty ratio of the power supplied to the heater 26 based on the heater heat generation amount computed by the heater heat generation amount computation section 53, and generates a PWM control signal corresponding to the duty ratio.

Using the power supplied from a power supply apparatus 59, the heater driver 57 energizes the heater 26, while controlling the energization based on the PWM control signal received from the PWM signal generation section 55. Thus, the heater 26 produces heat which is necessary to make the temperature of the gas sensor 8 approach the sensor target temperature or maintain the temperature of the gas sensor 8 at the sensor target temperature.

<1-2. Pump Current Control Processing>

Next, of the various types of control processing executed by the digital computation section 33, the pump current control processing will be described.

The pump current control processing is computation control processing for controlling the pump current Ip supplied to the pump cell 14 such that the detection voltage Vs of the electromotive force cell 24 becomes equal to a target control voltage (for example, 450 mV in the present embodiment).

Figure 2:
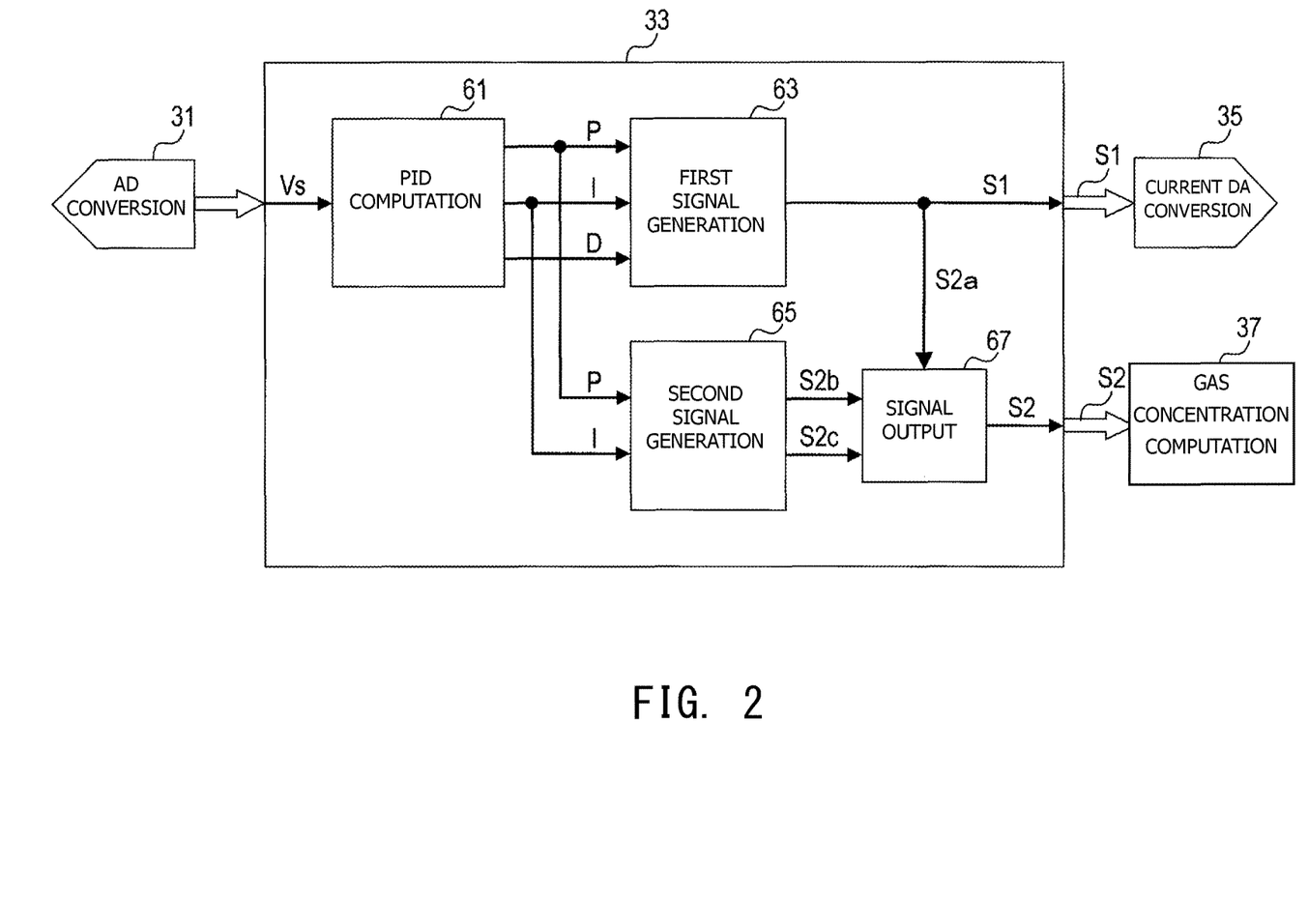
FIG. 2 is a functional block diagram of a digital computation section.

FIG. 2 shows a functional block diagram of the digital computation section 33 at the time when the digital computation section executes the pump current control processing.

The digital computation section 33 at the time when it executes the pump current control processing includes, as functional sections, a PID computation section 61, a first signal generation section 63, a second signal generation section 65, and a signal output section 67.

The PID computation section 61 performs PID computation processing (specifically, proportional computation processing, integral computation processing, and differential computation processing) based on the deviation $\Delta Vs$ between a target control voltage (450 mV) and the detection voltage Vs of the electromotive force cell 24 (the electromotive force of the electromotive force cell 24) by means of a digital circuit.

The first signal generation section 63 computes the supply control value for the pump current Ip supplied to the pump cell 14, based on a proportional computation result (P), an integral computation result (I), and a differential computation result (D) obtained as a result of the computation processing at the PID computation section 61, such that the deviation $\Delta Vs$ between the target control voltage (450 mV) and the detection voltage Vs of the electromotive force cell 24 (the electromotive force of the electromotive force cell 24) approaches 0 (in other words, such that the detection voltage Vs approaches the target control voltage).

The first signal generation section 63 produces a DAC control signal S1 which is a digital signal containing information regarding the current value and supply direction (forward direction or reverse direction) of the supply control value for the pump current Ip and is used for control of the pump current Ip. The first signal generation section 63 sends (outputs) the DAC control signal S1 to the current DA conversion section 35. Notably, the first signal generation section 63 sends the DAC control signal S1 as is to the signal output section 67 as a first gas detection signal S2a.

As described above, the current DA conversion section 35 having received the DAC control signal S1 converts the received digital signal (digital information) to an analog signal (i.e., performs DA conversion) and supplies to the pump cell 14 the pump current Ip determined based on the DAC control signal S1.

The second signal generation section 65 produces a second gas detection signal S2b and a third gas detection signal S2c based on the computation results obtained as a result of the computation processing at the PID computation section 61. The results of the computation by the PID computation section 61 change with the concentration of the particular gas (oxygen) contained in the exhaust gas.

The second signal generation section 65 of the present embodiment produces the second gas detection signal S2b based on the proportional computation result (P) and the integral computation result (I) among the proportional computation result (P), the integral computation result (I), and the differential computation result (D) output from the PID computation section 61, and produces the third gas detection signal S2c based on the integral computation result (I). The second signal generation section 65 sends the second gas detection signal S2b and the third gas detection signal S2c to the signal output section 67.

The signal output section 67 selects one of the first gas detection signal S2a, the second gas detection signal S2b, and the third gas detection signal S2c received from the first signal generation section 63 and the second signal generation section 65 in accordance with a predetermined setting. The signal output section 67 sends (outputs) the selected gas detection signal to the gas concentration computation section 37 as a gas detection signal S2 for detection of the concentration of the particular gas (oxygen) contained in the exhaust gas. The signal sent from the signal output section 67 to the gas concentration computation section 37 can be freely selected, for example, by changing the setting of the signal output section 67.

As described above, the gas concentration computation section 37 having received the gas detection signal S2 computes the concentration of the particular gas (oxygen) contained in the exhaust gas based on the gas detection signal S2 which contains the information computed at the digital computation section 33. Specifically, the gas concentration computation section 37 computes the concentration of the particular gas (oxygen) contained in the exhaust gas based on the information contained in the received gas detection signal S2 and the information contained in the stored past gas detection signal S2.

<1-3. Effects>

In the gas detection system 1 of the present embodiment, the sensor control apparatus 2 includes the AD conversion section 31, the digital computation section 33, and the current DA conversion section 35.

The digital computation section 33 at the time when it executes the pump current control processing includes the PID computation section 61, the first signal generation section 63, the second signal generation section 65, and the signal output section 67 as functional sections.

The PID computation section 61 performs PID computation processing (specifically, proportional computation processing, integral computation processing, and differential computation processing) based on the deviation $\Delta Vs$ between the target control voltage and the detection voltage Vs of the electromotive force cell 24 (the electromotive force of the electromotive force cell 24) by means of a digital circuit.

Based on the proportional computation result (P), the integral computation result (I), and the differential computation result (D) obtained as a result of the computation processing at the PID computation section 61, the first signal generation section 63 produces the DAC control signal S1 which is used for controlling the pump current Ip such that the detection voltage Vs of the electromotive force cell 24 assumes the predetermined reference value. The first signal generation section 63 sends (outputs) the DAC control signal S1 to the current DA conversion section 35, and sends the DAC control signal S1 as is to the signal output section 67 as the first gas detection signal S2a.

The second signal generation section 65 produces the second gas detection signal S2b based on the proportional computation result (P) and the integral computation result (I) among the proportional computation result (P), the integral computation result (I), and the differential computation result (D) obtained as a result of the computation processing at the PID computation section 61. The second signal generation section 65 produces the third gas detection signal S2c based on the integral computation result (I) among the proportional computation result (P), the integral computation result (I) and the differential computation result (D). The second signal generation section 65 sends (outputs) the second gas detection signal S2b and the third gas detection signal S2c to the signal output section 67.

The signal output section 67 selects one of the first gas detection signal S2a, the second gas detection signal S2b, and the third gas detection signal S2c, which are received from the first signal generation section 63 and the second signal generation section 65, in accordance with the predetermined setting. The signal output section 67 sends (outputs) the selected gas detection signal to the gas concentration computation section 37 as a gas detection signal S2 for detection of the particular gas (oxygen) contained in the exhaust gas. The gas concentration computation section 37 computes the concentration of the particular gas (oxygen) contained in the exhaust gas using the received gas detection signal S2.

Namely, the gas detection system 1 (the sensor control apparatus 2) can freely select an optimal gas detection signal from a plurality of types of gas detection signals (the first gas detection signal S2a, the second gas detection signal S2b, and the third gas detection signal S2c) in accordance with a user's need, application, or the like, and to output the selected gas detection signal to the gas concentration computation section 37 as the gas detection signal S2 used for gas detection. As a result, the degree of versatility of the gas detection system 1 (the sensor control apparatus 2) is increased.

For example, in the case where high responsiveness is required in the gas detection, it is advantageous to select and use, as the gas detection signal S2, the first gas detection signal S2a which is produced based on the three computation results (the proportional computation result (P), the integral computation result (I), and the differential computation result (D)) like the DAC control signal S1 used for control of the pump current Ip. In the case where noise reduction is desired, it is advantageous to select and use, as the gas detection signal S2, the second gas detection signal S2b which is produced based on the computation results, excluding the differential computation result (D) (the proportional computation result (P) and the integral computation result (I)). In the case where deterioration in responsiveness can be permitted to some degree and further reduction of noise is required, it is advantageous to select and use, as the gas detection signal S2, the third gas detection signal S2c which is produced based on the integral computation result (I). As described above, it becomes possible to select the gas detection signal S2 to be used for gas detection in accordance with a user's need, application, or the like. Therefore, the degree of versatility of the gas detection system 1 is increased.

Also, as described above, the first signal generation section 63 produces the DAC control signal S1 used for control of the pump current Ip based on the proportional computation result (P), the integral computation result (I), and the differential computation result (D) obtained as a result of the computation processing at the PID computation section 61. Therefore, by supplying to the pump cell 14 the pump current Ip generated based on the DAC control signal S1, the pumping (pumping out and pumping in) of oxygen by the pump cell 14 can be performed properly in accordance with the state of change in the electromotive force of the electromotive force cell 24.

As a result, in the gas detection system 1 (the sensor control apparatus 2), for the control of the pump current Ip of the pump cell 14 so as to render the detection voltage Vs of the electromotive force cell 24 coincident with the predetermined reference value, the DAC control signal S1 suitable for that control can be used, and for detection of the particular component (oxygen) contained in the exhaust gas (gas detection), an optimum gas detection signal can be freely selected from the plurality of types of gas detection signals (S2a, S2b, S2c) in accordance with a user's need, application, etc., and be used as the gas detection signal S2.

Also, since the gas detection system 1 (the sensor control apparatus 2) has the digital computation section 33 which is a digital control section (digital circuit), the work for design changes becomes easier as compared with the case where the gas detection system has an analog circuit. Therefore, it becomes easier to adapt to control of a greater number of types and control of gas sensors 8 having various characteristics. In particular, it is possible to easily realize a configuration which allows selective use of different types of gas detection signals as the gas detection signal S2 for gas detection in accordance with a user's need, application, etc.

Also, in the gas detection system 1 (the sensor control apparatus 2) of the present embodiment, the first signal generation section 63 and the second signal generation section 65 produce three types of gas detection signals (the first gas detection signal S2a, the second gas detection signal S2b, and the third gas detection signal S2c) based on the computation results including at least the integral computation result (I) among the proportional computation result (P), the integral computation result (I), and the differential computation result (D) obtained as a result of the computation processing at the PID computation section 61. Since each of the signals is based on the computation results including the integral computation result, the particular component (oxygen) contained in the exhaust gas can be detected accurately based on the state of change in the electromotive force of the electromotive force cell 24 over a long period of time.

As described above, the sensor control apparatus 2 of the present embodiment and the gas detection system 1 including the sensor control apparatus 2 allow selective use of gas detection signals for gas detection in accordance with a user's need, application, etc. Therefore, the sensor control apparatus 2 and the gas detection system 1 have a high degree of versatility.

<1-4. Corresponding Features in the Embodiment and Invention>

A description will be given of the corresponding features in the present embodiment and the invention.

The electromotive force cell 24 is an example of the detection cell of the invention; the pump cell 14 is an example of the oxygen pump cell of the invention; the gas sensor 8 is an example of the gas sensor of the invention; and the sensor control apparatus 2 is an example of the sensor control apparatus of the invention.

The PID computation section 61 of the digital computation section 33 is an example of the PID computation section of the invention; the first signal generation section 63 of the digital computation section 33 is an example of the feedback signal generation section of the invention; and the first signal generation section 63, the second signal generation section 65, and the signal output section 67 of the digital computation section 33 are examples of the gas detection signal generation section of the invention. The detection voltage Vs of the electromotive force cell 24 is an example of the electromotive force signal of the invention; the DAC control signal S1 is an example of the pump current control signal of the invention; and the gas detection signal S2 is an example of the gas detection signal of the invention.

The AD conversion section 31 is an example of the analog-to-digital conversion section of the invention; and the current DA conversion section 35 is an example of the digital-to-analog conversion section of the invention. The gas detection system 1 is an example of the gas detection system of the invention.

Other Embodiments

Although an embodiment of the present invention has been described, the present invention is not limited thereto, and the present invention can be implemented in various forms without departing from the scope of the present invention.

(1) In the above-described embodiment, the first signal generation section 63, the second signal generation section 65, and the signal output section 67, which constitute the gas detection signal generation section, produce the first gas detection signal S2a based on the proportional computation result (P), the integral computation result (I), and the differential computation result (D) among the results of the computation processing performed by the PID computation section 61, produce the second gas detection signal S2b based on the proportional computation result (P) and the integral computation result (I) among the results of the computation processing, and produce the third gas detection signal S2c based on the integral computation result (I) among the results of the computation processing. However, the gas detection signal generation section (the first signal generation section 63, the second signal generation section 65, and the signal output section 67) may produce these gas detection signals based on various combinations of the computation results other than the combinations mentioned above.

For example, the gas detection signal generation section (the first signal generation section 63, the second signal generation section 65, and the signal output section 67) may produce a gas detection signal based on the proportional computation result (P), or may produce a gas detection signal based on the differential computation result (D). Also, the gas detection signal generation section may produce a gas detection signal based on the proportional computation result (P) and the differential computation result (D), or may produce a gas detection signal based on the integral computation result (I) and the differential computation result (D).

(2) In the above-described embodiment, the first signal generation section 63 sends the DAC control signal S1 as is to the signal output section 67 as the first gas detection signal S2a. However, the first signal generation section 63 may be configured such that in accordance with, for example, an instruction from the signal output section 67, the first signal generation section 63 sends the DAC control signal S1 as is to the signal output section 67 as the first gas detection signal S2a.

(3) In the above-described embodiment, the second signal generation section 65 sends the second gas detection signal S2b and the third gas detection signal S2c to the signal output section 67. However, the second signal generation section 65 may be configured such that in accordance with, for example, an instruction from the signal output section 67, the second signal generation section 65 sends one of the second gas detection signal S2b and the third gas detection signal S2c to the signal output section 67.

(4) In the above-described embodiment, the signal output section 67 sends (outputs) a previously selected one of the first gas detection signal S2a, the second gas detection signal S2b, and the third gas detection signal S2c received from the first signal generation section 63, and the second signal generation section 65 to the gas concentration computation section 37 as the gas detection signal S2. However, the signal output section 67 may be configured to send (output) all the three signals to the gas concentration computation section 37. In such a case, the gas concentration computation section 37 selects one of the signals and computes the concentration of the particular gas (oxygen) contained in the exhaust gas based on the selected signal.

Figure 3:
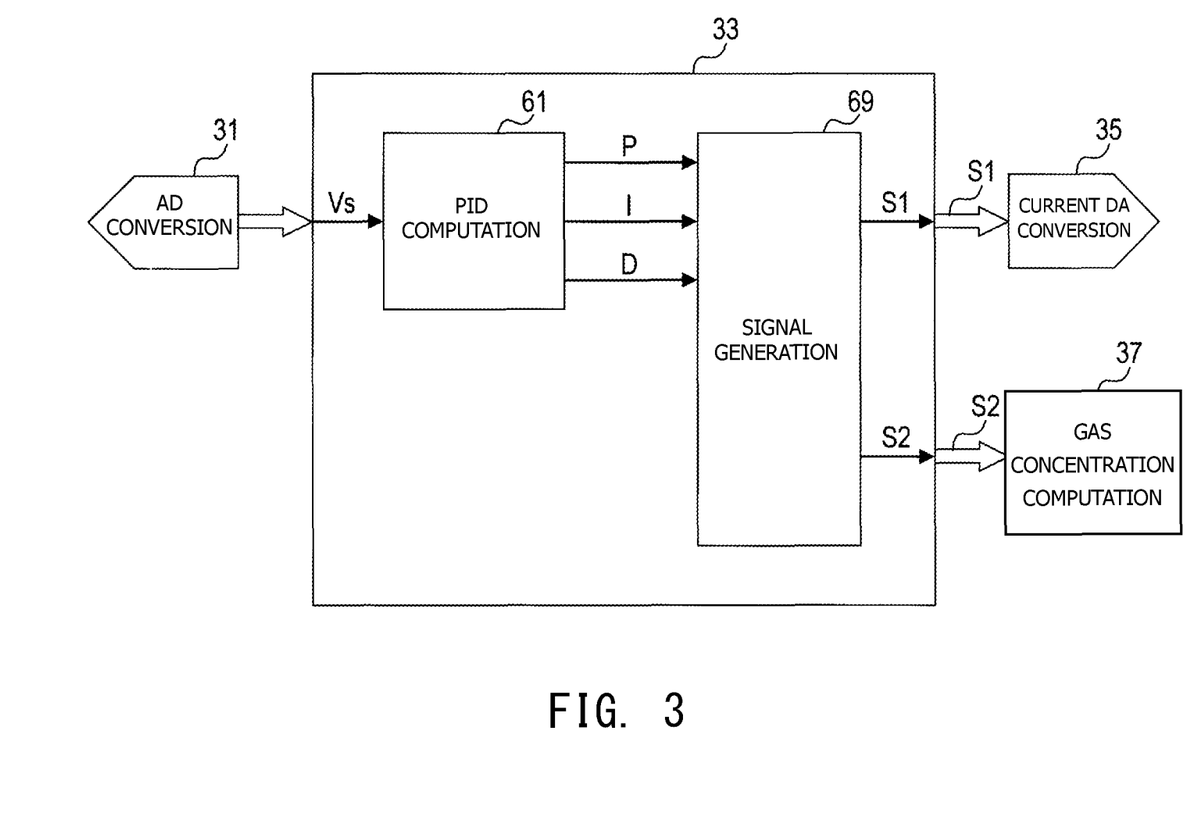
FIG. 3 is a functional block diagram of a digital computation section of another example.

(5) In the above-described embodiment, the digital computation section 33 includes the first signal generation section 63, the second signal generation section 65, and the signal output section 67 as independent functional sections. However, as shown in FIG. 3, the digital computation section 33 may include a signal generation section 69 including the functions of the first signal generation section 63, the second signal generation section 65, and the signal output section 67.

In the case of such a configuration, for example, the signal generation section 69 may produce the DAC control signal S1 based on the proportional computation result (P), the integral computation result (I), and the differential computation result (D) obtained as a result of the computation processing at the PID computation section 61, and send (output) the DAC control signal S1 to the current DA conversion section 35. Also, the signal generation section 69 may produce the gas detection signal S2 based on at least one computation result among the proportional computation result (P), the integral computation result (I), and the differential computation result (D) obtained as a result of the computation processing at the PID computation section 61, and send (output) the gas detection signal S2 to the gas concentration computation section 37.

(6) The present invention is not limited to a gas detection system and a sensor control apparatus which are used for the purpose of detecting a particular gas contained in exhaust gas discharged from an internal combustion engine, and may be used for the purpose of detecting a particular gas (e.g., oxygen) contained in intake gas introduced into an internal combustion engine or for the purpose of detecting a particular gas (e.g., oxygen) contained in an environmental gas.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2015-115835 filed Jun. 8, 2015, incorporated herein by reference in its entirety.

What is claimed is:

1. A sensor control apparatus for controlling a gas sensor including a detection cell which produces an electromotive force corresponding to a particular component contained in an object gas that has been introduced into an interior chamber of the gas sensor and an oxygen pump cell which pumps oxygen into or out of the object gas in accordance with pump current, the sensor control apparatus comprising:
    an analog-to-digital conversion section which converts an analog electromotive force signal changing with the electromotive force of the detection cell to a digital electromotive force signal;
    a PID computation section which digitally performs proportional computation processing, integral computation processing, and differential computation processing on the digital electromotive force signal;
    a pump current control signal generation section which generates a digital pump current control signal for controlling the pump current such that the digital electromotive force signal assumes a predetermined target value, based on the results of the proportional computation, the integral computation, and the differential computation performed by the PID computation section;
    a digital-to-analog conversion section which converts the digital pump current control signal to an analog signal; and
    a gas detection signal generation section configured to selectively set and produce a plurality of gas detection signals selected from (a) the proportional computation, the integral computation and the derivative computation performed by the HD computation section, (b) only the proportional computation and the integral computation performed by the PID computation section and (c) only the integral computation performed by the PID computation section for detection of the particular component contained in the object gas.

2. The sensor control apparatus as claimed in claim 1, wherein the gas detection signal generation section produces the gas detection signal based on the combination including at least the result of the integral computation among the results of the proportional computation, the integral computation, and the differential computation performed by the PID computation section.

3. A gas detection system comprising:
    a gas sensor including a detection cell which produces an electromotive force corresponding to a particular component contained in an object gas that has been introduced into an interior chamber of the gas sensor and an oxygen pump cell which pumps oxygen into or out of the object gas in accordance with a pump current; and
    the sensor control apparatus as claimed in claim 2.

4. A gas detection system comprising:
    a gas sensor including a detection cell which produces an electromotive force corresponding to a particular component contained in an object gas that has been introduced into an interior chamber of the gas sensor and an oxygen pump cell which pumps oxygen into or out of the object gas in accordance with a pump current; and
    the sensor control apparatus as claimed in claim 1.

* * * * *